United States Patent
Schumann

[19]

[11] Patent Number: 6,022,464
[45] Date of Patent: Feb. 8, 2000

[54] SENSOR FOR DETERMINING THE CONCENTRATION OF OXIDIZABLE ELEMENTS IN A GAS COMPOUND

[75] Inventor: Bernd Schumann, Rutesheim, Germany

[73] Assignee: Robert Bosch GmbH, Stuttgart, Germany

[21] Appl. No.: 09/011,577

[22] PCT Filed: May 16, 1997

[86] PCT No.: PCT/DE97/00996

§ 371 Date: Feb. 11, 1998

§ 102(e) Date: Feb. 11, 1998

[87] PCT Pub. No.: WO97/47963

PCT Pub. Date: Dec. 18, 1997

[30] Foreign Application Priority Data

Jun. 12, 1996 [DE] Germany ............... 196 23 434

[51] Int. Cl.[7] .................................................. G01N 27/26
[52] U.S. Cl. .................. 204/424; 204/291; 204/426; 204/429; 429/218.1
[58] Field of Search .................. 204/426, 425, 204/428, 429, 291, 292, 293; 429/218.1, 33, 190, 304; 205/425

[56] References Cited

U.S. PATENT DOCUMENTS

| | | | |
|---|---|---|---|
| 4,879,016 | 11/1989 | Joshi | 204/421 |
| 4,931,213 | 6/1990 | Cass | 252/507 |
| 5,023,153 | 6/1991 | Weppner | 429/40 |
| 5,037,525 | 8/1991 | Badwal | 204/421 |
| 5,443,711 | 8/1995 | Kojima et al. | 204/426 |
| 5,505,837 | 4/1996 | Friese et al. | 204/425 |
| 5,630,920 | 5/1997 | Friese et al. | 204/425 |
| 5,849,165 | 12/1998 | Kojima et al. | 204/426 |

FOREIGN PATENT DOCUMENTS 60-061654 4/1985 Japan.

*Primary Examiner*—Robert J. Warden, Sr.
*Assistant Examiner*—Kaj K. Olsen
*Attorney, Agent, or Firm*—Venable; George H. Spencer; Ashley J. Wells

[57] ABSTRACT

A sensor for determining the concentration of oxidizable constituents in a gas mixture includes a substrate which is planar and electrically insulating; a reference electrode which is positioned on a surface of the substrate and which catalyzes equilibrium adjustment of the gas mixture; a solid electrolyte which is ion-conducting and which is provided on at least the reference electrode; and at least one measuring electrode which is positioned on the ion-conducting solid electrolyte, which is one of not capable of catalyzing equilibrium adjustment of the gas mixture or is capable of catalyzing equilibrium adjustment of the gas mixture only to a small degree, which includes at least 50% of at least one of rutile and zirconium dioxide, and which is doped with acceptors and donors in which the acceptor contains at least one transition element, rare earth element, and mixtures thereof, and in which the donor is at least one of tantalum and niobium.

9 Claims, 1 Drawing Sheet

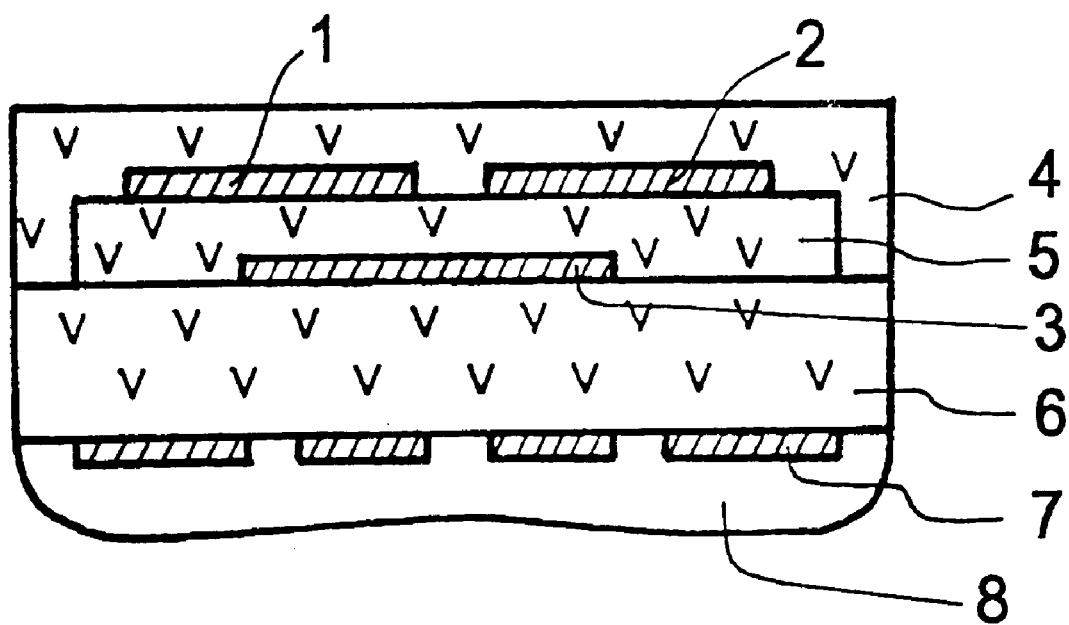

SENSOR FOR DETERMINING THE CONCENTRATION OF OXIDIZABLE ELEMENTS IN A GAS COMPOUND

BACKGROUND OF THE INVENTION

The invention is based on a sensor for determining the concentration of oxidizable constituents in a gas mixture, in particular for determining one or several of the gases NOx, CO, H2 and preferably unsaturated hydrocarbons, of the generic type as in the main claim. The exhaust gases from Otto and diesel motors, internal combustion engines and combustion plants can contain increased concentrations of oxidizable constituents, in particular NOx, CO, H2 and hydrocarbons, e.g., as a result of malfunctions of components such as an injection valve, or a as a result of an incomplete combustion. Thus, it is necessary to know the concentration of these exhaust-gas constituents to optimize the combustion reactions. A method for determining oxidizable gases is described in the JP-OS 60061654, according to which a stoichiometric conversion with oxygen takes place at a first measuring electrode of platinum metals, and according to which quasi equilibrium states are adjusted for the oxygen balance reaction at one or several additional metallic measuring electrodes with reduced catalytic activity. The Nernst voltages E1 and E2 are measured between the measuring electrodes and a reference electrode that is subjected to a reference gas with constant oxygen partial pressure, and their difference based on calibration curves is used to calculate the concentration of the gas constituents.

SUMMARY OF THE INVENTION

The present invention provides a sensor for determining the concentration of oxidizable constituents in a gas mixture, in particular for determining one or several of the gases $No_x$, $Co$, $H_2$, and preferably unsaturated hydrocarbons, for which a reference electrode that catalyzes the equilibrium adjustment of the gas mixture, an ion-conducting solid electrolyte, and at least one measuring electrode that is subjected to the measuring gas and which cannot or only to a small degree catalyze the equilibrium adjustment of the gas mixture are arranged in superimposed layers on one of the large surfaces of a planar, electrically insulating substrate, characterized in that the measuring electrode contains one or several semiconductors as the main component. In contrast, the sensor according to the invention, has improved analytical performance characteristics, in particular an increased sensitivity and selectivity relative to individual measuring gas constituents to be determined.

Advantageous modifications and improvements of the sensor specified in the main claim are possible through the measures listed in the dependent claims. Preferably, the sensor has two measuring electrodes which are arranged side by side and at a distance to each other on the solid electrolyte. Preferably, the semiconductor of the sensor is doped with acceptors and/or donors. Preferably, the semiconductor is an oxide or a single-phase or multi-phase mixed oxide, in particular a rutile or dirutile or a mixture thereof. The semiconductor preferably consists of titanium oxide. Preferably, the donor is present in a higher concentration than the acceptor. Preferably, the donor is an element with higher valence than the metal or metals forming the semiconductor. Preferably, the donor is tantalum and/or niobium. Preferably the semiconductor contains one or several transition elements as acceptor, in particular nickel, copper, cobalt and/or chromium, preferably nickel, copper and/or cobalt and/or rare earths. Preferably, the acceptor is contained in the semiconductor as solid solution or as segregated constituent. Preferably, the semiconductor contains donors and/or acceptors in a concentration of respectively 0.01 to 25%. More preferably, the semiconductor contains 0.5 to 15% niobium and 0.25 to 7% nickel, preferably 7% niobium and 3% nickel.

The sensitivity and selectivity of the measuring electrodes are improved through doping of the in particular oxidic or mixed oxidic semiconductors with acceptors and/or donors. The conductivity of the measuring electrodes is improved by adding donors, especially at higher concentrations as compared to the acceptors. Particularly efficient electrodes are obtained if the acceptor is selected from the series of transition metals and/or rare earths and/or if the donor is one or both of the elements tantalum and niobium.

An increased miniaturization, a simpler design and a more cost-effective production are achieved by sintering the solid electrolyte such that it is porous. As a result of this, no reference gas must be supplied, which leads to a considerable simplification of the probe design.

The thermodynamic equilibrium is advantageously adjusted in the solid electrolyte already by selecting a catalytically effective solid-electrolyte material. It must be viewed as a particular advantage here that the gases interfering with the reference signal can be oxidized purposefully, which simplifies the signal evaluation or makes it possible at all.

It is also useful if the measuring electrodes as well as the solid electrolyte are porous, which further improves the diffusion of the measuring gas molecules to the reference electrode. The electrode adhesion and thus also the service life of the sensor can be improved by adding admixtures to the solid electrolyte in the regions adjoining the electrodes.

BRIEF DESCRIPTION OF THE DRAWINGS

The invention is described with more detail in the following with the aid of a drawing and an exemplary embodiment. FIG. 1 shows a section through a sensor according to the invention.

DESCRIPTION OF THE PREFERRED EMBODIMENTS

FIG. 1 shows a section of a sensor according to the invention. A reference electrode 3, e.g. made of platinum, a solid electrolyte 5, measuring electrodes 1 and 2 as well as a gas-permeable protective layer 4 are deposited in superimposed layers on one of the large surfaces of an electrically insulating, planar, ceramic substrate 6. A heating device 7 with cover 8 is deposited on the opposite-arranged large substrate surface.

In order to determine the concentration of oxidizable constituents in exhaust gases, the sensor is heated with the heating device 7 to a temperature between 300 and 1000° C., preferably to 600° C.

The solid electrolyte can be sintered to be porous in order to permit the diffusion of the measuring gas to the reference electrode and the adjustment of the oxygen equilibrium potential. However, the person skilled in the art can also select other solutions known to him/her, e.g. via a reference channel or a reference gas atmosphere.

Above the oxygen-ion conducting solid electrolyte, the sensor generates a cell voltage on at least one measuring electrode by means of a first half-cell reaction, adjusted with the aid of the reference electrode, and by means of a second half-cell reaction that is influenced by the oxidizable gas constituents to be determined. The concentrations of the gas constituents are determined from the voltage values, via calibration curves.

The sensor according to the invention therefore can be used in the most simple case with a reference electrode, which catalyzes the equilibrium adjustment of the gas mixture and a measuring electrode, which can catalyze the equilibrium adjustment of the gas mixture only slightly or not at all. However, it is also possible to deposit two measuring electrodes, as shown in FIG. 1, or even several measuring electrodes with respectively different catalytic activity for adjusting the oxygen equilibrium states. As referred to the reference electrode, the measuring electrodes in that case react with a varying voltage, which depends on the type of gas.

With arrangements having two or more measuring electrodes with varied catalytic activity, it is also possible to evaluate the voltages between the measuring electrodes for determining oxidizable gases. In addition, the Seebeck effect is omitted for voltage measurements between electrodes that are arranged in the same plane and at the same distance to the heating device, e.g. the electrodes 1 and 2 in FIG. 1. Furthermore, arrangements with at least two measuring electrodes provide the option of compensating the lateral sensitivity of a first measuring electrode completely or at least in part through the signal from an additional measuring electrode, in that the sensitivity of this additional measuring electrode is correspondingly adjusted to the interfering gas constituents.

In accordance with another embodiment, the solid electrolyte is configured in such a way, e.g. by adding 0.01 to 10% volume platinum, that the solid electrolyte catalytically converts the gases to be measured, so that only the gases corresponding to the thermodynamic balance arrive at the reference electrode or that the solid electrolyte converts only the gases that interfere with the reference signal.

In accordance with another alternative, one or several measuring electrodes are designed to be porous in addition to the solid electrolyte, which facilitates the gas diffusion to the reference electrode.

Semiconductors with a high specific sensitivity for certain oxidizable gases are used as measuring electrode materials. Particularly suitable are oxides or mixed oxides, in particular on a rutile or dirutile base or mixtures thereof, which may be doped with acceptors and/or donors. It is advantageous if titanium and/or zirconium dioxide are used.

Suitable donors are in particular tantalum and niobium, preferably elements with a higher valence than the metals which form the semiconductor. Suitable acceptors are transition metals, in particular nickel, copper, cobalt and/or chromium, preferably nickel, copper and/or cobalt, as well as rare earths. The acceptor in this case can be contained in the semiconductor as a fixed solution or as a segregated constituent.

The concentrations of acceptors and donors respectively are in the range of 0.01 to 25%. With lower percentages, no improvements of the characteristics of the measuring electrodes are achieved and with higher percentages, lattice defects appear.

The high sensitivity of, for example, titanium oxide doped with acceptors and donors, especially for unsaturated hydrocarbons, is conditional upon the adsorptive interaction of the orbitals for the Pi-bonds of the unsaturated hydrocarbons with the electron-attracting acceptor sites on the semiconductor surface.

It is advantageous if a conductivity-increasing donor is added to the electrode, in particular at a higher concentration than the acceptor, to prevent the share of the acceptor that reduces the conductivity from becoming fully effective electronically.

The following example describes a production method for a sensor according to the invention:

A 30 $\mu$m thick screen printing layer of a rutile doped with 7% niobium and 3% of one of the transition metals nickel, copper or iron, is printed onto a substrate containing a reference electrode, e.g. made of platinum, and this is covered by a solid electrolyte layer. A heating device is deposited on the opposite side of the substrate. The sensor is sintered at 1200° C. for 90 minutes with a heating/cooling ramp of 300° C./hour. Following the sintering, the solid electrolyte has pore sizes ranging from 10 nm to 100 $\mu$m. The voltage is measured at the cell, structured in this way, at a 1 MOhm resistor between the reference and the rutile electrode with the aid of a platinum conductor track, mounted such that it is insulated against the solid electrolyte and contacts only the measuring electrode. The sensor is thereby heated with a heating device to 600° C.

A simulated exhaust gas, containing 10% oxygen, 5% water and 5% carbon dioxide as well as 30 ppm sulphur dioxide, is used as measuring gas. Oxidizable gases are added in the amounts specified in the table.

The last line of the following table lists the voltage values for a mixed-potential electrode of 20% gold and 80% platinum, which represents a state of the technology measuring electrode, for a comparison.

Table: Voltage values (in mv) in dependence on the concentration of oxidizable gases and the composition of the measuring electrode.

| rutile electrode comparison electrode with 7% Nb and 3% | Voltages in mv | | | |
|---|---|---|---|---|
| oxidizabie gases (ppm) | Ni | Cu | Fe | 20% Au and 80% Pt |
| propene 460 | 150 | 45 | 60 | 320 |
| 180 | 120 | 36 | 47 | 280 |
| 90 | 90 | 27 | 35 | 180 |
| H2 460 | 30 | 12 | 20 | 500 |
| 180 | 17 | 6 | 10 | 450 |
| 90 | 5 | 3 | 4 | 380 |
| CO 460 | 40 | 3 | 16 | 70 |
| 180 | 15 | — | 7 | 35 |
| 90 | 7 | — | 6 | 23 |

The table shows that a rutile semiconductor electrode with 7% niobium as donor and 3% nickel as acceptor has the highest selectivity for propylene as conducting substance. In contrast, the gold/platinum system known from the state of the technology displays a particularly high lateral sensitivity to hydrogen.

What is claimed is:

1. A sensor for determining the concentration of oxidizable constituents in a gas mixture, comprising:
    a substrate which is planar and electrically insulating;
    a reference electrode which is positioned on a surface of the substrate and which catalyzes equilibrium adjustment of the gas mixture;
    a solid electrolyte which is ion-conducting and which is provided on at least the reference electrode; and
    at least one measuring electrode which is positioned on the ion-conducting solid electrolyte, which is one of not capable of catalyzing equilibrium adjustment of the gas mixture or is capable of catalyzing equilibrium adjustment of the gas mixture only to a small degree, which comprises at least 50% of at least one of rutile and zirconium dioxide, and which is doped with acceptors and donors in which the acceptor contains at least one transition element, rare earth element, and mixtures thereof, and in which the donor is at least one of tantalum and niobium.

2. The sensor according to claim 1, wherein two measuring electrodes are provided, and wherein the two measuring electrodes are arranged side by side and at a distance from one another on the solid electrolyte.

3. The sensor according to claim 1, wherein the donor has a concentration which is greater than that of the acceptor.

4. The sensor according to claim 1, wherein the acceptor contains at least one transition element selected from the group consisting of nickel, copper, chromium and cobalt.

5. The sensor according to claim 1, wherein the acceptor is contained in the at least are measuring electrode as one of (a) a solid solution or (b) as a segregated constituent.

6. The sensor according to claim 1, wherein the donor has a concentration of 0.01%, and wherein the acceptor has a concentration of 25%.

7. The sensor according to claim 1, wherein the at least one measuring electrode contains from 0.5% to 15% of niobium and from 0.25% to 7% of nickel.

8. The sensor according to claim 1, wherein the at least one measuring electrode contains 7% niobium and 3% nickel.

9. The sensor according to claim 1, wherein the sensor determines the concentration of at least one gas selected from the group consisting of $NO_x$, CO, $H_2$ and unsaturated hydrocarbons.

* * * * *